(12) United States Patent
Yamamoto (10) Patent No.: US 7,649,627 B2
(45) Date of Patent: Jan. 19, 2010

(54) WAVELENGTH CALIBRATION METHOD AND WAVELENGTH CALIBRATION APPARATUS

(75) Inventor: Toshikazu Yamamoto, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 528 days.

(21) Appl. No.: 11/703,643

(22) Filed: Feb. 8, 2007

(65) Prior Publication Data
US 2007/0195318 A1    Aug. 23, 2007

(30) Foreign Application Priority Data
Feb. 17, 2006    (JP)    ............... 2006-041082

(51) Int. Cl.
  *G01J 3/26* (2006.01)
(52) U.S. Cl. ...................................... 356/326
(58) Field of Classification Search ............ 356/326
See application file for complete search history.

(56) References Cited

U.S. PATENT DOCUMENTS

| | | | |
|---|---|---|---|
| 6,441,900 B1 * | 8/2002 | Fujiyoshi | ............ 356/300 |
| 6,452,674 B1 * | 9/2002 | Fujiyoshi | ............ 356/328 |
| 2001/0019410 A1 * | 9/2001 | Kojima | ............ 356/334 |
| 2006/0170919 A1 * | 8/2006 | Takahashi et al. | ............ 356/328 |

FOREIGN PATENT DOCUMENTS

JP    2000-283841 A    10/2000

* cited by examiner

*Primary Examiner*—Kara E Geisel
(74) *Attorney, Agent, or Firm*—Sughrue Mion, PLLC (57) ABSTRACT

In a wavelength calibration method, an observed spectrum of a light that has a wavelength band is obtained, wherein the light has at least an attenuated wavelength component that corresponds to at least a predetermined absorption wavelength that is included in the wavelength band. A corrected spectrum is then obtained from the observed spectrum, wherein the corrected spectrum has reduced dependencies upon the full width at half maximum of an emission band of the light and upon an intensity ripple period of the light.

16 Claims, 5 Drawing Sheets

UNPROCESSED SPECTRUM OF OBSERVATION

FIG. 6

CORRECTED SPECTRUM OF OBSERVATION
AFTER MOVING AVERAGE PROCESS IS PERFORMED

FIG. 7

CORRECTED SPECTRUM OF OBSERVATION
AFTER RESOLUTION IS CHANGED

WAVELENGTH CALIBRATION METHOD AND WAVELENGTH CALIBRATION APPARATUS

BACKGROUND OF THE INVENTION

1. Field of the Invention

The present invention generally relates to a wavelength calibration method and a wavelength calibration apparatus.

Priority is claimed on Japanese Patent Application No. 2006-041082, filed Feb. 17, 2006, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

Japanese Unexamined Patent Application, First Publication, No. 2000-283841 discloses a conventional wavelength calibration technique to be used in an optical spectrum analyzer. This conventional wavelength calibration technique will be described as follows. A light emitting diode is performed as a reference light source to emit a reference light with a predetermined wavelength band toward a gas absorption cell. The gas absorption cell causes light absorptions at particular wavelengths that correspond to reference wavelengths, thereby obtaining an observed spectrum. The observed spectrum indicates absorption wavelengths as observation wavelengths.

The absorption wavelengths as observation wavelengths are then compared to the above-described particular wavelengths as reference wavelengths to detect a difference as an error between them at each wavelength. The wavelength calibration of the optical spectrum analyzer is performed based on the average of the detected errors for the particular wavelengths. If the absorption wavelengths as observation wavelengths are identical to the particular wavelengths as reference wavelengths, this means that the wavelength measured by the optical spectrum analyzer has no error. If the absorption wavelengths are different from the particular wavelengths, this means that the measured wavelength has an error. The wavelength calibration of the optical spectrum analyzer is performed so that the absorption wavelengths as observation wavelengths become identical to the particular wavelengths as reference wavelengths.

The above-described conventional wavelength calibration technique performs the wavelength calibration based on the average of plural errors at plural particular wavelengths, thereby further reducing the calibration error. Namely, the above-described conventional wavelength calibration technique can improve the accuracy of wavelength measurement as compared to another conventional technique that performs wavelength calibration based on an error at a single particular wavelength.

Further, the wavelength calibration can be performed by using the light emitting diode as a light source. It has been well known that the light emitting diode includes a semiconductor chip disposed between an anode and a cathode. The light emitting diode may cause an interference of the emitted light in the semiconductor chip. The interference of the emitted light may cause a ripple in intensity of the emitted light in the wavelength band. The ripple may cause errors of the absorption wavelengths.

The light emitting diode may have an overall unevenness or non-flatness of the light intensity distribution in the wavelength band. The overall unevenness of the light intensity distribution may cause further errors of the absorption wavelengths.

In view of the above, it will be apparent to those skilled in the art from this disclosure that there exists a need for an improved apparatus and/or method. This invention addresses this need in the art as well as other needs, which will become apparent to those skilled in the art from this disclosure.

SUMMARY OF THE INVENTION

Accordingly, it is a primary object of the present invention to provide a wavelength calibration method.

It is another object of the present invention to provide a wavelength calibration method free from the above disadvantages.

It is a further object of the present invention to provide a wavelength calibration method free from any causes for errors in wavelength measurement when a light emitting diode is used as a light source.

It is a still further object of the present invention to provide a wavelength calibration method that is capable of realizing a highly accurate wavelength calibration.

It is yet a further object of the present invention to provide a wavelength calibration apparatus.

It is an additional object of the present invention to provide a wavelength calibration apparatus free from the above disadvantages.

It is another object of the present invention to provide a wavelength calibration apparatus free from any causes for errors in wavelength measurement when a light emitting diode is used as a light source.

It is still another object of the present invention to provide a wavelength calibration apparatus that is capable of realizing a highly accurate wavelength calibration.

In accordance with a first aspect of the present invention, a wavelength calibration method may include, but is not limited to, the following processes. An observed spectrum of a light that has a wavelength band may be obtained, wherein the light has at least an attenuated wavelength component that corresponds to at least a predetermined absorption wavelength that is included in the wavelength band. A corrected spectrum may be obtained from the observed spectrum, wherein the corrected spectrum has reduced dependencies upon the full width at half maximum of an emission band of the light and upon an intensity ripple period of the light. A wavelength calibration may be performed with reference to the corrected spectrum.

In accordance with a second aspect of the present invention, a wavelength calibration apparatus may include, but is not limited to, an optical system and a control system. The optical system may be configured to obtain a wavelength-separated light from a light. The light has a wavelength band, wherein the light has at least an attenuated wavelength component that corresponds to at least a predetermined absorption wavelength that is included in the wavelength band. The control system may be configured to obtain an observed spectrum of the light from the wavelength-separated light, the control system being configured to obtain a corrected spectrum from the observed spectrum, wherein the corrected spectrum has reduced dependencies upon the full width at half maximum of an emission band of the light and upon an intensity ripple period of the light. The control system may be configured to perform a wavelength calibration with reference to the corrected spectrum.

BRIEF DESCRIPTION OF THE DRAWINGS

Referring now to the attached drawings which form a part of this original disclosure.

DETAILED DESCRIPTION OF THE INVENTION

In accordance with a first aspect of the present invention, a wavelength calibration method may include, but is not limited to, the following processes. An observed spectrum of a light that has a wavelength band may be obtained, wherein the light has at least an attenuated wavelength component that corresponds to at least a predetermined absorption wavelength that is included in the wavelength band. A corrected spectrum may be obtained from the observed spectrum, wherein the corrected spectrum has reduced dependencies upon the full width at half maximum of an emission band of the light and upon an intensity ripple period of the light. A wavelength calibration may be performed with reference to the corrected spectrum. The reduction of the dependencies upon the full width at half maximum of an emission band of the light and upon an intensity ripple period of the light may improve the accuracy in wavelength calibration.

In some cases, the corrected spectrum may be substantially independent from the full width at half maximum and from the intensity ripple period. Substantial independencies from the full width at half maximum and from the intensity ripple period may further improve the accuracy in wavelength calibration.

In some cases, the wavelength calibration may, for example, be performed by the following processes. At least a difference between the at least a predetermined absorption wavelength and at least an absorption wavelength of the corrected spectrum may be obtained. The wavelength calibration may be performed based on the difference.

In some cases, the light may have a plurality of attenuated wavelength components that corresponds to a plurality of predetermined absorption wavelengths that is included in the wavelength band. In this case, a plurality of differences between the plurality of predetermined absorption wavelengths and a plurality of absorption wavelengths of the corrected spectrum may be obtained. The wavelength calibration may be performed based on the plurality of differences.

In some cases, the corrected spectrum may be obtained by the following processes. A moving average process of the observed spectrum may be performed to obtain a moving average spectrum. A ratio between the moving average spectrum and the observed spectrum may be calculated.

In other cases, the corrected spectrum may be obtained by the following processes. A different observed spectrum of the light may be obtained at a different wavelength resolution that is larger than the full width at half maximum and smaller than a half of the intensity ripple period. The different wavelength resolution is different from a wavelength resolution at which the observed spectrum is obtained. A ratio between the different observed spectrum and the observed spectrum may be calculated.

In some cases, the observed spectrum may be obtained by the following processes. The light is emitted from a light emitting diode. The light may be transmitted through a gas absorption cell that is configured to absorb the light at the at least a predetermined absorption wavelength. The gas absorption cell may be filled with a gas that has a plurality of predetermined absorption wavelengths. A typical example of the gas may include, but is not limited to, an acetylene gas. The wavelength calibration may be performed by the following processes. At least two differences between at least two absorption wavelengths of the plurality of predetermined absorption wavelengths and at least two absorption wavelengths of the corrected spectrum may be obtained. The wavelength calibration may be performed based on the at least two differences.

In accordance with a second aspect of the present invention, a wavelength calibration apparatus may include, but is not limited to, an optical system and a control system. The optical system may be configured to obtain a wavelength-separated light from a light. The light has a wavelength band. The light has at least an attenuated wavelength component that corresponds to at least a predetermined absorption wavelength that is included in the wavelength band. The control system may be configured to obtain an observed spectrum of the light from the wavelength-separated light, the control system being configured to obtain a corrected spectrum from the observed spectrum, wherein the corrected spectrum has reduced dependencies upon the full width at half maximum of an emission band of the light and upon an intensity ripple period of the light. The control system may be configured to perform a wavelength calibration with reference to the corrected spectrum. The reduction of the dependencies upon the full width at half maximum of an emission band of the light and upon an intensity ripple period of the light may improve the accuracy in wavelength calibration.

The corrected spectrum may be substantially independent from the full width at half maximum and from the intensity ripple period. Substantial independencies from the full width at half maximum and from the intensity ripple period may further improve the accuracy in wavelength calibration.

In some cases, the control system may be configured to obtain at least a difference between the at least a predetermined absorption wavelength and at least an absorption wavelength of the corrected spectrum. The control system may also be configured to perform the wavelength calibration based on the difference.

In some cases, the light may have a plurality of attenuated wavelength components that corresponds to a plurality of predetermined absorption wavelengths that is included in the wavelength band. The control system may be configured to obtain a plurality of differences between the plurality of predetermined absorption wavelengths and a plurality of absorption wavelengths of the corrected spectrum. The control system may be configured to perform the wavelength calibration based on the plurality of differences.

In some cases, the control system may be configured to perform a moving average process of the observed spectrum to obtain a moving average spectrum. The control system is configured to calculate a ratio between the moving average spectrum and the observed spectrum.

In other cases, the control system may be configured to obtain a different observed spectrum of the light at a different wavelength resolution that is larger than the full width at half maximum and smaller than a half of the intensity ripple period. The different wavelength resolution is different from a wavelength resolution at which the observed spectrum is obtained. The control system may also be configured to calculate a ratio between the different observed spectrum and the observed spectrum.

In some cases, the optical system may further include, but is not limited to, a light emitting diode that emits the light, a gas absorption cell, a spectrometer, and an optical detector. The gas absorption cell may be disposed to allow the light to be transmitted through the gas absorption cell. The gas absorption cell may be configured to absorb the light at the at least a predetermined absorption wavelength. The spectrometer may be configured to convert the light that has been transmitted through the gas absorption cell into a wavelength-separated light that has wavelength components. The optical detector may be configured to detect the intensity of the wavelength-separated light to generate a light intensity detection signal.

In some cases, the gas absorption cell may be filled with a gas that has a plurality of predetermined absorption wavelengths. A typical example of the gas may include, but is not limited to, an acetylene gas. The control system may be configured to obtain at least two differences between at least two absorption wavelengths of the plurality of predetermined absorption wavelengths and at least two absorption wavelengths of the corrected spectrum. The control system may be configured to perform the wavelength calibration based on the at least two differences.

Selected embodiments of the present invention will now be described with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
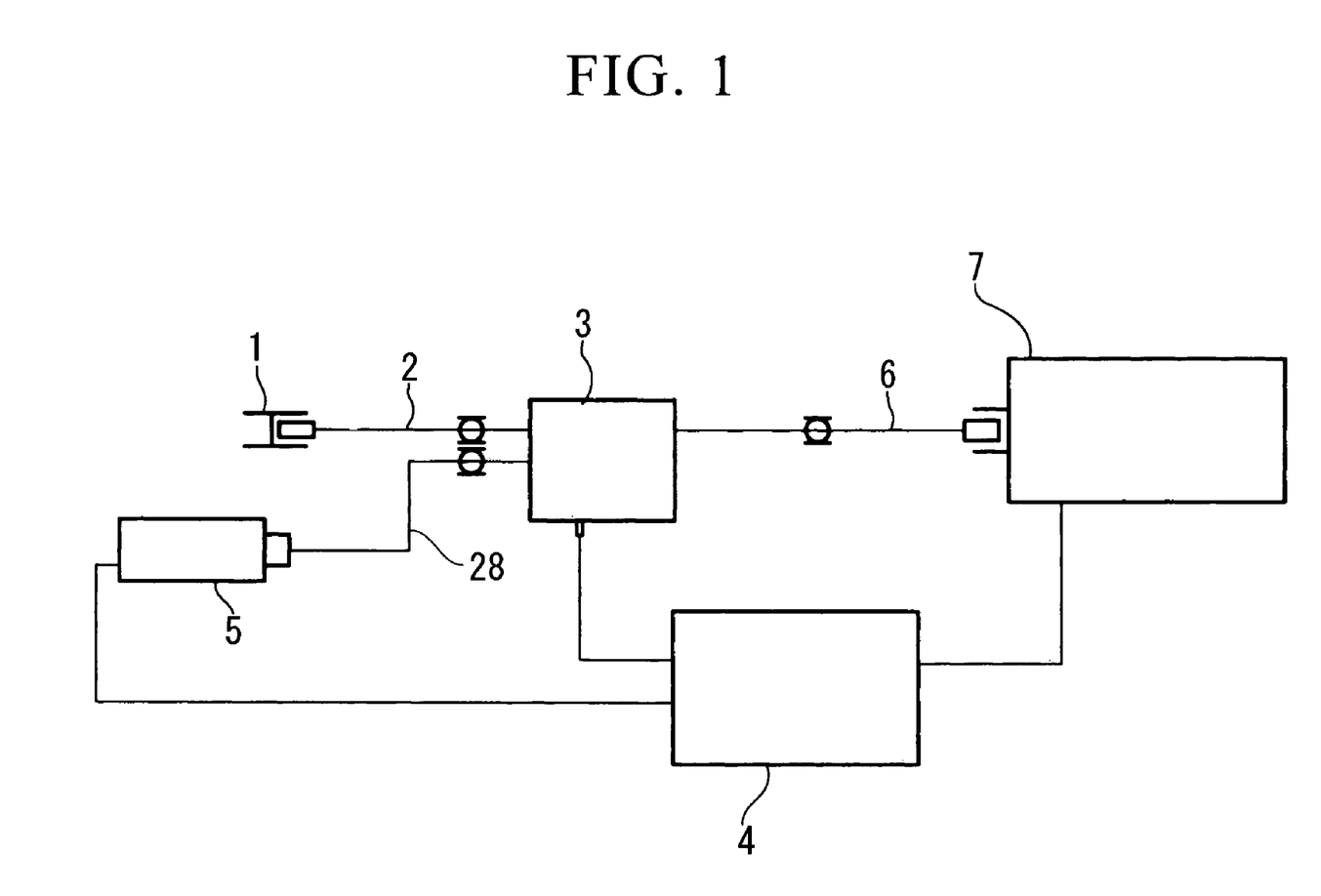
FIG. 1 is a schematic block diagram illustrating the configuration of an optical spectrum analyzer in accordance with an embodiment of the present invention.

FIG. 1 is a schematic block diagram illustrating the configuration of an optical spectrum analyzer in accordance with an embodiment of the present invention. The optical spectrum analyzer may include, but is not limited to, optical fibers 2 and 28, an optical switch 3, a control unit 4, a reference light source 5, an optical fiber 6 and a spectrum analyzing unit 7. The optical fiber 2 has a light incident side 1.

The light incident side 1 may be configured to receive an incidence of a measured light. The measured light is a light that is subject to a measurement of wavelength thereof. The optical switch 2 may include first and second optical incident ports and an optical outgoing port. The optical fiber 2 connects between the light incident side 1 and the first optical incident port of the optical switch 3. The incident light travels from the light incident side 1 through the optical fiber 2 to the first optical input of the optical switch 3. The reference light source 5 has an emitting port.

The reference light source 5 is electrically connected to the control unit 4. The reference light source 5 is configured to generate and emit a reference light under the control of the control unit 4. The optical fiber 28 connects between the emitting port of the reference light source 5 and the second optical incident port of the optical switch 3. The light emitted from the reference light source 5 travels through the optical fiber 28 to the second optical incident port of the optical switch 3.

The optical switch 3 is electrically connected to the control unit 4. The optical switch 3 is configured to select one of the first and second optical incident ports and optically connect the selected optical incident port to the optical outgoing port under the control of the control unit 4. The optical switch 3 is configured to output the selected one of the incident light and the reference light from the optical outgoing port thereof.

The optical spectrum analyzing unit 7 has an optical incident port. The optical spectrum analyzing unit 7 is electrically connected to the control unit 4. The optical fiber 6 connects between the optical outgoing port of the optical switch 3 to the optical incident port of the optical spectrum analyzing unit 7. The optical spectrum analyzing unit 7 is configured to perform an optical spectrum analysis of the selected light under the control of the control unit 4.

Figure 2:
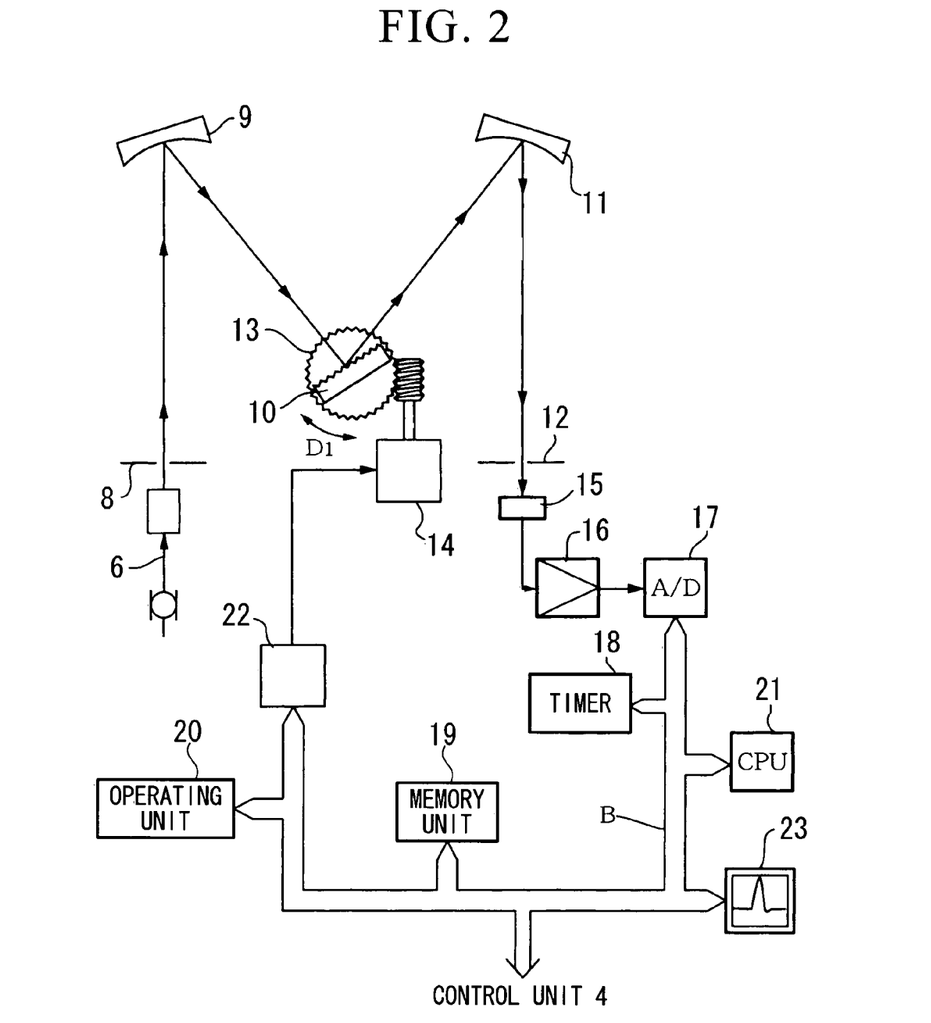
FIG. 2 is a schematic diagram illustrating the configuration of an optical spectrum analyzing unit included in the optical spectrum analyzer shown in FIG. 1.

FIG. 2 is a schematic diagram illustrating the configuration of the optical spectrum analyzing unit 7 included in the optical spectrum analyzer shown in FIG. 1. The optical spectrum analyzing unit 7 may include, but is not limited to, an optical system and a control system. The optical system may mainly include, but is not limited to, a spectrometer. The spectrometer may be realized by the Czerney-Turner spectrometer. The Czerney-Turner spectrometer may include, but is not limited to, an incoming slit 8, a first mirror 9, a diffraction grating 10, a second mirror 11, and an outgoing slit 12.

The incoming slit 8 is disposed in the optical incident port of the optical spectrum analyzing unit 7. The incoming slit 8 is configured to limit a wavelength band of an incident light that has traveled or propagated through the optical fiber 6. The first mirror 9 may be realized by, but is not limited to, a concave mirror. The first mirror 9 is disposed to be distanced from the incoming slit 8. The first mirror 9 is also disposed to be directed so that the first mirror 9 reflects, toward the diffraction grating 10, the incident light that has been transmitted through the incoming slit 8.

The diffraction grating 10 is disposed to be distanced from the first mirror 9. The diffraction grating 10 is configured to receive the reflected incident light from the first mirror 9. The diffraction grating 10 is configured to spatially separate the incident light into spectral components that have different wavelengths and are spatially separated, thereby generating a wavelength-separated beam of light. The wavelength-separated beam of light has spectral components that have different wavelengths and are spatially separated. The wavelength-separated beam of light is traveled toward the second mirror 11.

The diffraction grating 10 may be disposed on a rotary stage 13. The rotary stage 13 is configured to rotate in directions shown in an arrow mark "D1". Rotation of the rotary stage 13 changes the angle of the diffraction grating 10 with reference to the reflected incident light that has been transmitted from the first mirror 9. The rotary stage 13 may be mechanically engaged with a gear that is fixed to a rotary shaft of a motor 14. The rotary stage 13 may be driven by the motor 14. The motor 14 may be realized by, but is not limited to, a stepping motor. The angle of the diffraction grating 10 with reference to the reflected incident light defines a wavelength selected by the Czerney-Turner spectrometer. In other words, the selected wavelength depends on the angle of the diffraction grating 10 with reference to the reflected incident light. This angle may be calibrated periodically or unperiodically in accordance with the wavelength calibration process.

The second mirror 11 may also be realized by, but is not limited to, a concave mirror. The second mirror 11 is disposed to be distanced from the diffraction grating 10. The second mirror 11 is also disposed to be directed so that the second mirror 11 reflects, toward the outgoing slit 12, the wavelength-separated beam of light that has been transmitted from the diffraction grating 10.

The outgoing slit 12 is disposed to be distanced from the second mirror 11 and allow a portion of the wavelength-separated beam of light to pass through it. The outgoing slit 12 is configured to limit the wavelength band of the wavelength-separated beam of light that has been transmitted from the second mirror 11. As described above, the wavelength-separated beam of light has spectral components that have different wavelengths and are spatially separated. The width of the outgoing slit 12 defines the wavelength band of a portion of the wavelength-separated beam of light, wherein the portion passes through the outgoing slit 12. In other words, the width of the outgoing slit 12 limits the wavelength band of the outgoing beam of light that passes through the outgoing slit 12.

As described above, the optical spectrum analyzing unit 7 may include the optical system and the control system. The control system may include, but is not limited to, an optical detector 15, an amplifier 16, an analog-to-digital converter 17, a timer 18, a memory 19, an operating unit 20, a central processing unit (CPU) 21, a motor driving circuit 22, and a display unit 23.

The optical detector 15 may be disposed to receive the outgoing beam of light that has passed through the outgoing slit 12. The optical detector 15 may be realized by, but is not limited to, a photodiode. The optical detector 15 may be configured to perform a photoelectric conversion of the outgoing beam of light into a detected signal as an electrical signal that indicates the intensity of the outgoing beam of light.

The amplifier 16 may be electrically connected to the optical detector 15. The amplifier 16 may be configured to receive the detected signal from the optical detector 15 and amplify the detected signal, thereby generating an amplified signal.

The analog-to-digital converter 17 may be electrically connected to the amplifier 16. The analog-to-digital converter 17 may be configured to receive the amplified signal from the amplifier 16 and perform an analog-to-digital conversion of the amplified signal, thereby generating a set of data that is related to a detected light intensity. The set of data indicates the intensity of the outgoing beam of light having been transmitted through the outgoing slit 12. The set of data will be referred to as light intensity detection data.

The central processing unit (CPU) 21 is connected to the analog-to-digital converter 17 through a bus "B" so that the CPU 21 receives the light intensity detection data from the analog-to-digital converter 17. The timer 18 is also connected to the CPU 21 through the bus "B". The timer 18 clocks the date and time, thereby generating a timer signal that indicates information related to the date and time. The CPU 21 receives the timer signal from the timer 18.

The memory 19 is configured to store a control program, a signal processing program and a wavelength calibration program. Those programs are executed by the CPU 21. Program codes are read out of the memory 18 and supplied to the CPU 21 under the control of the CPU 21. The operating unit 20 provides a user interface between a user and the CPU 21. The operating unit 20 is connected to the CPU 21 through the bus "B". The operating unit 20 is configured to receive the entry of the operating instructions from a user. The operating unit 20 is also configured to transmit the user's instructions to the CPU 21 through the bus "B". The operating unit 20 may have operation keys such as function keys and ten keys.

The display unit 23 is connected to the CPU 21 through the bus "B". The motor driving circuit 22 is connected to the motor 14. The motor driving circuit 22 is also connected to the CPU 21 through the bus "B". The CPU 21 is also connected through the bus "B" to the control unit 4 that is shown in FIG. 1.

The CPU 21 is connected through the bus "B" to the analog-to-digital converter 17, the timer 18, the memory 19, the operating unit 20, the motor driving circuit 22, and the display unit 23. The CPU 21 is configured to execute the control program and control the analog-to-digital converter 17, the timer 18, the memory 19, the operating unit 20, the motor driving circuit 22, and the display unit 23.

The CPU 21 is also configured to receive the light intensity detection data from the analog-to-digital converter 17. The CPU 21 is also configured to execute the signal processing program and apply a variety of process to the light intensity detection data, thereby producing processed light intensity detection data as a result of observation. In general, the processed light intensity detection data include one or more observed spectrums. The CPU 21 sends the processed light intensity detection data to the display unit 23 so that the display unit 23 displays the observed spectrum or spectrums.

In some cases, the CPU 21 may be configured to control the motor driving circuit 22 based on the control program, thereby controlling the angle of the diffraction grating 10. The CPU 21 may be configured to perform a predetermined set of process of the light intensity detection data, based on the signal processing program, thereby obtaining the processed light intensity detection data including the observed spectrum or spectrums as the result of observation. The CPU 21 renders the display unit 23 display the observed spectrum or spectrums.

The CPU 21 may be configured to receive, from the timer 18, the timer signal that indicates information related to the date and time. The CPU 21 may be configured to execute the wavelength calibration program and perform a wavelength calibration of the optical spectrum analyzer with reference to the timer signal. In some cases, the CPU 21 may perform the wavelength calibration when a predetermined time has lapsed after a power is applied to the optical spectrum analyzer. In other cases, the CPU 21 may perform the wavelength calibration at a time interval that has been set by an operator, for example, every hour or every day.

The motor driving circuit 22 is configured to drive the motor 14 under the control of the CPU 21.

The display unit 23 may be realized by a known display device, for example, a cathode ray tube (CRT) or a liquid crystal display (LCD). The display unit 23 may be configured to receive image information including the processed light intensity detection data from the CPU 21. The display unit 23 may be configured to display one or more observed spectrums included in the processed light intensity detection data.

Figure 3:
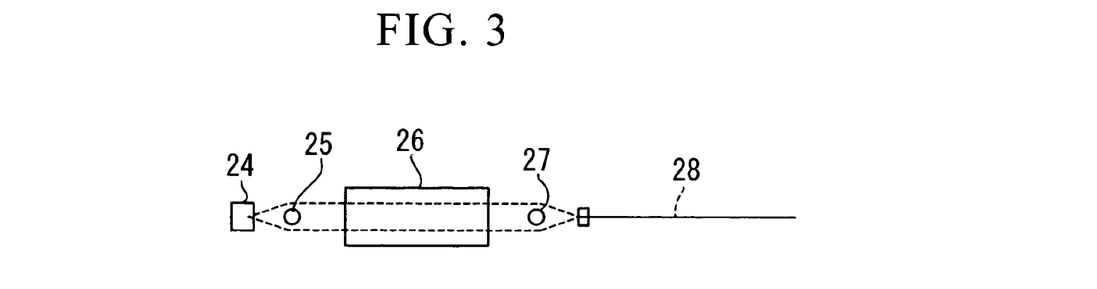
FIG. 3 is a diagram illustrating the configuration of a reference light source included in the optical spectrum analyzer shown in FIG. 1.

FIG. 3 is a diagram illustrating the configuration of the reference light source 5 included in the optical spectrum analyzer shown in FIG. 1. As described above, the reference light source 5 is electrically connected to the control unit 4. The reference light source 5 is configured to generate or emit a reference light under the control of the control unit 4. The reference light source 5 is optically coupled to the optical fiber 28 so that the emitted reference light then propagates through the optical fiber 28. The reference light source 5 may include, but is not limited to, a light emitting diode 24, a collimate lens 25, a gas absorption cell 26, and a condenser lens 27.

The light emitting diode 24 has a light emitting diode chip such as a semiconductor chip. A driving current as a direct current is applied to the light emitting diode chip under the control of the control unit 4, whereby the light emitting diode 24 emits a reference light that has a predetermined emission band. The emitted reference light is a divergent beam of reference light. The emitted reference light is transmitted to the collimate lens 25. The collimate lens 25 converts the divergent beam of reference light into a parallel beam of reference light. The parallel beam of reference light is then transmitted through the gas absorption cell 26.

The gas absorption cell 26 may be realized by a light transmittable cell that is filled with an optical absorption gas. The optical absorption gas absorbs light at a specific absorption wavelength or wavelengths. In some cases, an acetylene gas may be used as the optical absorption gas. The acetylene gas has a predetermined plurality of absorption wavelengths. However, the absorption wavelengths may vary depending on the temperature of the gas absorption cell 26. In some cases, the gas absorption cell 26 may advantageously be contained in a temperature-controlled container so that the gas absorption cell 26 is maintained at a predetermined temperature so as to fix the absorption wavelengths. The reference light is observed at the predetermined plurality of absorption wavelengths by the gas absorption cell 26, thereby forming a cell-transmitted beam of reference light. The cell-transmitted beam of reference light is then transmitted to the condenser lens 27.

The condenser lens 27 condenses the cell-transmitted beam of reference light, thereby generating a condensed beam of reference light. The condensed beam of reference light is incident into the optical fiber 28. The reference light then propagates through the optical fiber 28 to the optical switch 3.

Operations of the optical spectrum analyzer and particularly wavelength calibration operations will be described.

The optical spectrum analyzer has a normal measurement mode, in which operations are performed as follows. The CPU 21 in the optical spectrum analyzing unit 7 executes the control program and supplies control instructions to the control unit 4. In accordance with the control instructions, the control unit 4 sets the optical switch 3 so that the optical switch 3 selects the first optical incident port that is optically connected with the optical fiber 2 having the light incident side 1. In other words, the optical switch 3 selects an observation light that has been transmitted through the optical fiber 2, but does not select the reference light that has been transmitted through the optical fiber from the reference light source 5. The optical switch 3 outputs the observation light and allows the output of the observation light to be transmitted through the optical fiber 6 to the optical spectrum analyzing unit 7.

The observation light is incident into the optical spectrum analyzing unit 7 which has the configuration described above with reference to FIG. 2. Namely, the beam of observation light is incident into the above-described Czerney-Turner spectrometer of the optical spectrum analyzing unit 7. As described above, the Czerney-Turner spectrometer generates a wavelength-separated beam of observation light that has spectral components, wherein the spectral components have different wavelengths and are spatially separated. A portion of the wavelength-separated beam of observation light passes through the outgoing slit 12. The passing portion of the wavelength-separated beam of observation light is then incident into the optical detector 15.

The passing portion of the wavelength-separated beam of observation light has one or more specific wavelengths. The wavelength or wavelengths of the passing portion of the wavelength-separated beam of observation light can be varied by varying the angle of the diffraction grating 10. The optical detector 15 receives the passing portion of the wavelength-separated beam of observation light. The optical detector 15 detects each wavelength component of the wavelength-separated beam of observation light sequentially, thereby generating a detection signal for each wavelength component thereof.

The detection signal for each wavelength component is then supplied to the amplifier 16. The detection signal is amplified by the amplifier 16. The amplified detection signal is then supplied to the analog-to-digital converter 17. The amplified detection signal is converted into light intensity detection data by the analog-to-digital converter 17. The light intensity detection data is then supplied to the CPU 21. The light intensity detection data is processed by the CPU 21. The processed light intensity detection data includes one or more observed spectrums. The processed light intensity detection data is supplied to the display unit 23 so that one or more observed spectrums are displayed by the display unit 23. The observed spectrum indicates the intensity of a wavelength component of the observation light, provided that the wavelength component is within the predetermined wavelength band for observation. The wavelength band for observation may have been set by the operating unit 20.

The following descriptions will be directed to the wavelength calibration processes that are performed by the above-described optical spectrum analyzer.

When a predetermined time has elapsed from a time of applying a power to the optical spectrum analyzer or from when the instructions to perform the calibration process is entered from the operating unit 20, the CPU 21 executes the control program and shifts the optical spectrum analyzer from the above-described normal measurement mode into a wavelength calibration mode. In the wavelength calibration mode, the CPU 21 executes the wavelength calibration program and performs calibration processes.

Figure 4:
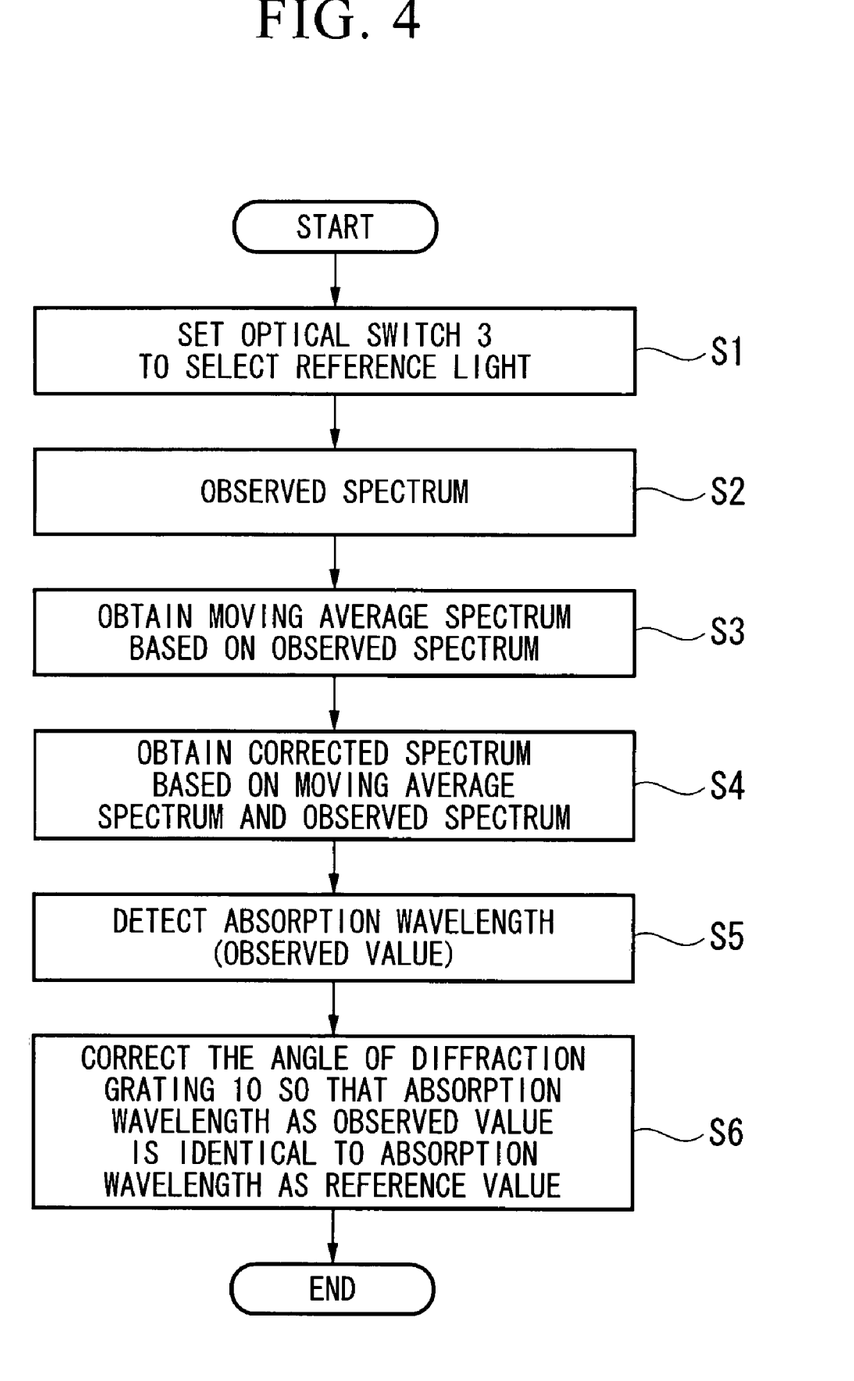
FIG. 4 is a flow chart illustrating a typical example of the calibration process performed by an optical spectrum analyzing unit included in the optical spectrum analyzer shown in FIG. 1.

FIG. 4 is a flow chart illustrating a typical example of the calibration processes performed by the optical spectrum analyzing unit 7 included in the optical spectrum analyzer shown in FIG. 1.

In Step S1, the CPU 21 gives the control unit 4 the instructions to control the reference light source 5 so that the control unit 4 places the light emitting diode 24 from the non-emission state into the emission state. The CPU 21 also gives the control unit 4 the control instructions, in accordance with which the control unit 4 sets the optical switch 3 to select the reference light that has been emitted from the reference light source 5. The reference light is then outputted from the optical switch 3 and transmitted through the optical fiber 6 to the optical spectrum analyzing unit 7. As described above, the reference light source 5 includes the gas absorption cell 26 shown in FIG. 3. The reference light passes through the gas absorption cell 26. The cell-transmitted light is then emitted from the reference light source 5.

In Step S2, the cell-transmitted beam of reference light is incident into the optical spectrum analyzing unit 7. The cell-transmitted beam of reference light is incident into the above-described Czerney-Turner spectrometer of the optical spectrum analyzing unit 7. As described above, the Czerney-Turner spectrometer generates a wavelength-separated beam of reference light that has spectral components, wherein the spectral components have different wavelengths and are spatially separated. A portion of the wavelength-separated beam of reference right passes through the outgoing slit 12. This portion of the wavelength-separated beam of reference light will be referred to as a passing portion. The passing portion of the wavelength-separated beam of reference light is then incident into the optical detector 15.

The passing portion of the wavelength-separated beam of reference light has one or more specific wavelengths. The wavelength or wavelengths of the passing portion of the wavelength-separated beam of reference light can be varied by varying the angle of the diffraction grating 10. The optical detector 15 is configured to receive the passing portion of the wavelength-separated beam of reference light. The optical detector 15 is also configured to detect each wavelength component of the wavelength-separated beam of reference light sequentially, thereby generating a detection signal for each wavelength component thereof.

The detection signal for each wavelength component is then supplied to the amplifier 16. The detection signal is amplified by the amplifier 16. The amplified detection signal is then supplied to the analog-to-digital converter 17. The amplified detection signal is converted into light intensity detection data by the analog-to-digital converter 17. The light intensity detection data is then supplied to the CPU 21. The light intensity detection data is processed by the CPU 21. The processed light intensity detection data includes one or more observed spectrums. The processed light intensity detection data is supplied to the display unit 23 so that one or more observed spectrums are displayed by the display unit 23. The observed spectrum indicates the intensity of a wavelength component of the reference light.

As described above, the light emitting diode 24 emits a beam of reference light that has a predetermined emission band. The emitted beam of reference light is transmitted through the gas absorption cell 26, in which the intensity of the beam of reference light is selectively attenuated at specific wavelengths that correspond to the predetermined absorption wavelengths of the acetylene gas that is filled in the gas absorption cell 26. In other words, the specific wavelength components of the beam of reference light are attenuated, wherein the specific wavelength components correspond to the predetermined absorption wavelengths of the acetylene gas. The cell-transmitted beam of reference light has the attenuated wavelength components.

As described above, an interference of the beam of reference light may be caused in the semiconductor chip of the light emitting diode. The interference of the beam of reference light may cause a ripple in intensity of the emitted beam of light in the wavelength band. The intensity distribution of the beam of reference light is not flat and has a predetermined full width at half maximum in the wavelength band. Namely, the beam of reference light as emitted from the light emitting diode has a ripped and non-flat intensity distribution. Thus, the cell-transmitted light also has the rippled and non-flat intensity distribution. The ripple and the non-flatness of the intensity distribution may cause an error or errors in detecting absorption wavelengths of the acetylene gas from the light intensity detection data. The error or errors may deteriorate the accuracy of the wavelength calibration.

Figure 5:
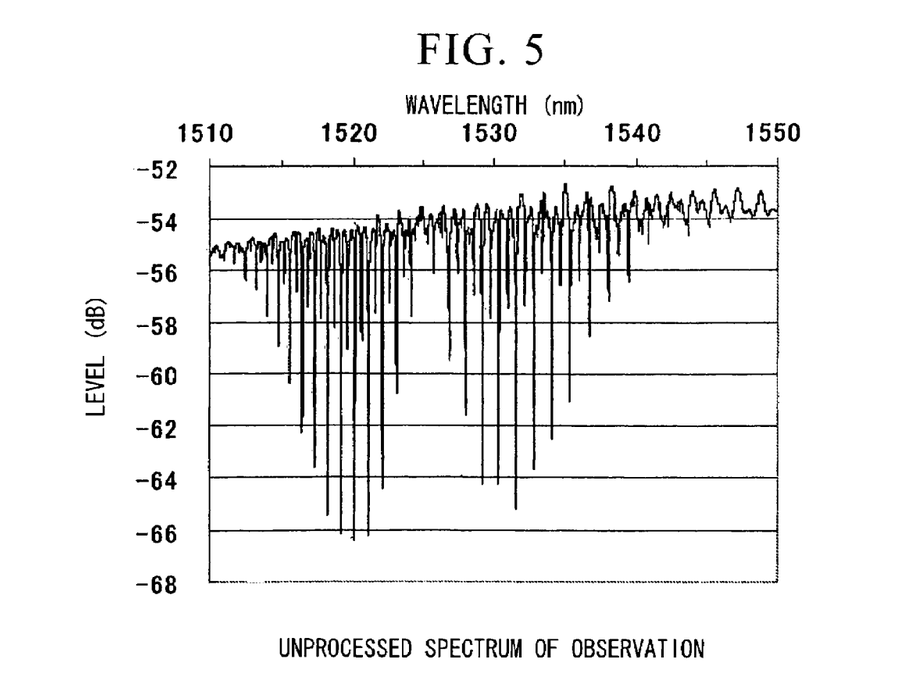
FIG. 5 is a view illustrating an observed spectrum of a cell-transmitted light, wherein the spectrum was observed in the normal measurement mode.

FIG. 5 is a view illustrating an observed spectrum of the cell-transmitted beam of light, wherein the spectrum was observed in the normal measurement mode and over a wavelength band of 1510 nm to 1550 nm. The observed spectrum shows that the cell-transmitted beam of reference light has the ripple at a period of 1 nm to 2 nm, and also has the full width at half maximum in the range of 10 nm to 100 nm. The observed spectrum also shows that the cell-transmitted beam of reference light has an intensity distribution that has a generally gentle slope over the wavelength band of 1510 nm to 1550 nm. The intensity distribution has steeply attenuated wavelength components which correspond to the absorption wavelengths of the acetylene gas. The steeply attenuated wavelength components have the full width at half maximum of approximately 0.02 nm.

The full width at half maximum of 0.02 nm of the steeply attenuated wavelength components is much narrower than the full width at half maximum of 10 nm to 100 nm of the emission band of the beam of reference light and also much narrower than 1 nm to 2 nm period of the ripple. The ripple is caused by the interference in the semiconductor chip of the light emitting diode. The optical spectrum analyzer is configured to perform the wavelength calibration processes by utilizing differences among the full width at half maximum of approximately 0.02 nm of the absorption wavelengths, the other full width at half maximum of 10 nm to 100 nm of the emission band of the reference light, and the ripple period of 1 nm to 2 nm. The wavelength calibration processes correct or compensate the error or errors that are caused by the non-flatness of the emission band of the reference light and by the ripple due to the interference appearing in the semiconductor chip of the light emitting diode.

In Step S3, the CPU 21 applies a moving average process to the observed spectrum that is derived from the light intensity detection data obtained in Step S2, thereby obtaining a moving average spectrum from the observed spectrum.

In Step S4, the CPU 21 calculates a ratio of the moving average spectrum to the observed spectrum and obtains a corrected spectrum that is free of the above described error factor factors.

The corrected spectrum can theoretically be described below. The spectrum $T(\lambda)$ of the reference light that is emitted from the reference light source 5 is a synthesized spectrum of an emission spectrum $L(\lambda)$ given by the light emitting diode 24 and an absorption spectrum $G(\lambda)$ of the gas absorption cell 26. This synthesized spectrum is given by the following equation (1).

$$T(\lambda) = G(\lambda) \cdot L(\lambda) \tag{1}$$

The absorption spectrum $G(\lambda)$ has an extremely steep property. The absorption spectrum $G(\lambda)$ can be expressed by using both the absorption efficiency "k" and the delta function $\delta(\lambda - \lambda_o)$, where $\lambda_o$ is the absorption wavelength. The absorption spectrum $G(\lambda)$ is given by the following equation (2).

$$G(\lambda) = 1 - k \cdot \delta(\lambda - \lambda_o) \tag{2}$$

The equation (2) is incorporated into the equation (1), thereby obtaining the equation (3) that gives the spectrum $T(\lambda)$ of the reference light.

$$T(\lambda) = G(\lambda) \cdot L(\lambda) \tag{3}$$
$$= [1 - k \cdot \delta(\lambda - \lambda_o)] \cdot L(\lambda)$$

Assuming that a wavelength filtering property $F_1(\lambda)$ of the optical spectrum analyzing unit 7 is sufficiently narrower than the emission spectrum $L(\lambda)$ of the light emitting diode 24 and that the wavelength filtering property $F_1(\lambda)$ is suitable to observe the absorption spectrum $G(\lambda)$ of the gas absorption cell 26, then the wavelength filtering property $F_1(\lambda)$ can be expressed by using the delta function $\delta(\lambda - \lambda_s)$, where $\lambda_s$ is the filter center frequency. The wavelength filtering property $F_1(\lambda)$ is thus given by the following equation (4).

$$F_1(\lambda) = \delta(\lambda - \lambda_s) \tag{4}$$

Therefore, the observed spectrum $S_1(\lambda)$ to be observed by the optical spectrum analyzing unit 7 is based on the above-described equations (3) and (4). Thus, the observed spectrum $S_1(\lambda)$ is given by the following equation (5).

$$S_1(\lambda) = T(\lambda) \cdot F_1(\lambda) \quad (5)$$
$$= [1 - k \cdot \delta(\lambda - \lambda_o)] \cdot L(\lambda) \cdot \delta(\lambda - \lambda_s)$$
$$= \delta(\lambda - \lambda_s) \cdot L(\lambda) - k \cdot \delta(\lambda - \lambda_o) \cdot \delta(\lambda - \lambda_s) \cdot L(\lambda)$$

The following relationships (6) can be established based on the equation (5) by using a relationship between the absorption wavelength ($\lambda_o$) and the filter center frequency ($\lambda_s$).

If $\lambda = \lambda_s = \lambda_o$, then $S_1(\lambda) = (1-k) \cdot L(\lambda)$ If $\lambda = \lambda_s \neq \lambda_o$, then $S_1(\lambda) = L(\lambda)$ If $\lambda \neq \lambda_s \neq \lambda_o$, then $S_1(\lambda) = 0$ \quad (6)

The filter center frequency ($\lambda_s$) may be set based on the angle of the diffraction grating 10. Thus, the observed spectrum $S_1(\lambda)$ can be expressed by the following equation (7).

If $\lambda = \lambda_o$, then $S_1(\lambda) = (1-k) \cdot L(\lambda)$

If $\lambda \neq \lambda_o$, then $S_1(\lambda) = L(\lambda)$ \quad (7)

The observed spectrum $S_1(\lambda)$ is subject to the moving average process, where samplings are taken over the range of $-N/2$ to $+N/2$ at the center of the target wavelength ($\lambda$). In this case, the total number of samplings is (N+1). This moving average process is applied to the observed spectrum $S_1(\lambda)$, thereby obtaining a moving average spectrum $S_2(\lambda)$ that is expressed by the following equation (8).

$$S_2(\lambda) = \frac{1}{N+1} \sum_{n=-N/2}^{+N/2} S_1(\lambda_n) \quad (8)$$

The moving average spectrum $S_2(\lambda)$ can be given by the following equation (9) when the absorption wavelength ($\lambda_o$) is present or absent in the wavelength section over which the moving average process is performed.

$$S_2(\lambda) = \begin{cases} \dfrac{1}{N+1}[L(\lambda_{N/2}) + \ldots + L(\lambda_{N/2})] & \text{ABSORPTION SPECTRUM IS ABSENT} \\ & \text{IN MOVING AVERAGE SECTION} \\ \dfrac{1-k}{N+1} L(\lambda_0) + \dfrac{1}{N+1}\begin{bmatrix} L(\lambda_{-N/2}) + \ldots + L(\lambda_{a-1}) + \\ L(\lambda_{a+1}) + \ldots + L(\lambda_{+N/2}) \end{bmatrix} & \text{ABSORPTION SPECTRUM IS PRESENT} \\ & \text{IN MOVING AVERAGE SECTION}(\lambda_0 = \lambda_a) \end{cases} \quad (9)$$

It is hereby assumed that the product of the interval of sampling and the number of sampling in the moving average process is sufficiently smaller than both the full width at half maximum of 10 nm to 100 nm of the emission band of the reference light and the ripple period of 1 nm to 2 nm. Under this assumption, the moving average spectrum $S_2(\lambda)$ can be given by the following equation (10) in either case where the absorption wavelength ($\lambda_o$) is present or absent in the wavelength section over which the moving average process is performed.

$$S_2(\lambda) \approx \begin{cases} L(\lambda) & \text{ABSORPTION SPECTRUM IS ABSENT IN} \\ & \text{THE SECTION OF } n - N/2 \text{ to } n + N/2 \\ \dfrac{1-k}{1+N} L(\lambda_0) + \dfrac{N}{1+N} L(\lambda) & \text{ABSORPTION SPECTRUM IS PRESENT IN} \\ & \text{THE SECTION OF } n - N/2 \text{ to } n + N/2 \end{cases} \quad (10)$$

A corrected spectrum $S_3(\lambda)$ is hereby introduced, wherein the corrected spectrum $S_3(\lambda)$ is given by a ratio of the observed spectrum $S_1(\lambda)$ to the moving average spectrum $S_2(\lambda)$. Assuming that the constant N that defines the number of sampling is sufficiently larger than 1, the corrected spectrum $S_3(\lambda)$ can be approximated to the following equation (11) in the first to third cases as follows. In the first case, the absorption wavelength ($\lambda_o$) is absent in the wavelength section over which the moving average process is performed. In the second case, the absorption wavelength ($\lambda_o$) is present in the wavelength section over which the moving average process is performed, provided that the target wavelength ($\lambda$) is different from the absorption wavelength ($\lambda_o$). In the third case, the absorption wavelength ($\lambda_o$) is present in the wavelength section over which the moving average process is performed, provided that the target wavelength ($\lambda$) is identical to the absorption wavelength ($\lambda_o$).

$$S_3(\lambda) = \frac{S_1}{S_2} = \begin{cases} 1 & \text{ABSORPTION SPECTRUM IS ABSENT IN} \\ & \text{THE SECTION OF } n-N/2 \text{ to } n+N/2 \\ \dfrac{\left(1+\dfrac{1}{N}\right)L(\lambda)}{\dfrac{1-k}{N}L(\lambda_o)+L(\lambda)} \approx 1 & \text{ABSORPTION SPECTRUM IS PRESENT IN} \\ & \text{THE SECTION OF } n-N/2 \text{ to } n+N/2 \\ \dfrac{\left(1+\dfrac{1}{N}\right)L(\lambda)}{\dfrac{1-k}{N}L(\lambda_o)+L(\lambda)} \approx (1-k): & \begin{array}{l} \lambda \neq \lambda_o \\ \lambda = \lambda_o \end{array} \end{cases} \quad (11)$$

The equation (11) shows that the corrected spectrum $S_3(\lambda)$ depends on "1" or the absorption coefficient "k" and also that the corrected spectrum $S_3(\lambda)$ is independent from the emission spectrum $L(\lambda)$ of the light emitting diode 24. Namely, the equation (11) shows that the corrected spectrum $S_3(\lambda)$ is independent from both the full width at half maximum of approximately 10 nm to 100 nm of the emission band of the reference light and the ripple period of 1 nm to 2 nm.

Figure 6:
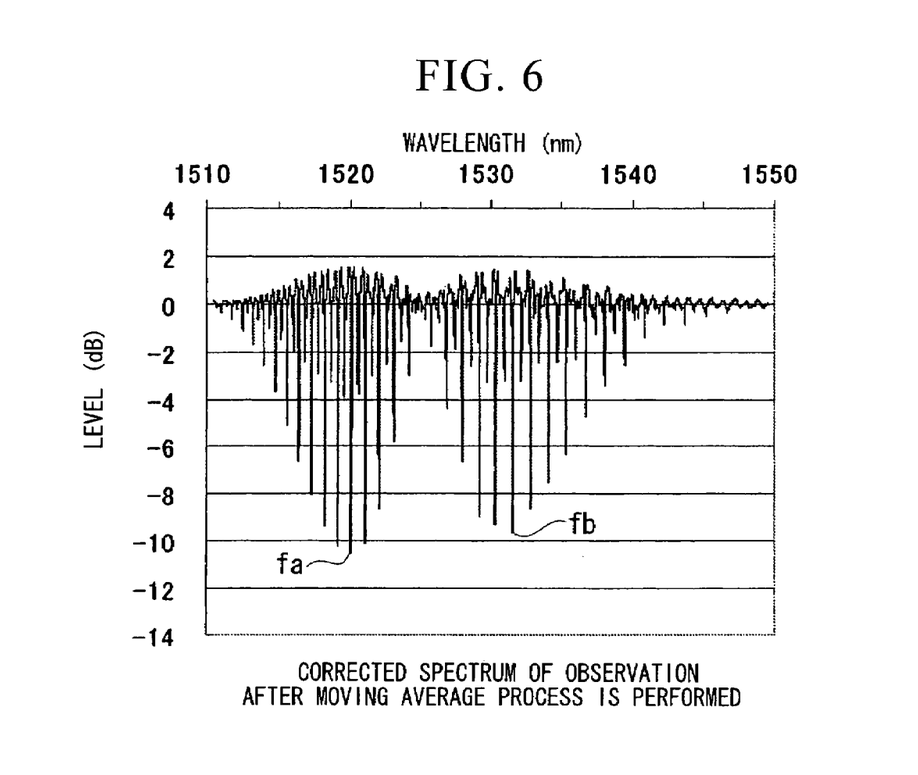
FIG. 6 is a view illustrating a corrected spectrum that is obtained by correcting the observed spectrum of FIG. 5.

FIG. 6 is a view illustrating a corrected spectrum that is obtained by correcting the observed spectrum of FIG. 5. The corrected spectrum has an intensity distribution that has two gentle hillocks. The corrected spectrum is free of the above-described ripple of 1 nm to 2 nm and the slope.

In Step S5, the CPU 21 detects absorption wavelengths at which extremely large and steep attenuations appear in the corrected spectrum, wherein the corrected spectrum is independent from both the full width at half maximum of the emission band of the reference light and the ripple period.

In Step S6, the CPU 21 calculates a difference of the detected absorption wavelengths from the reference values for absorption wavelengths. The reference values for absorption wavelengths have been stored in the memory 19. The CPU 21 corrects the control instructions for the motor driving circuit 22 so that the detected absorption wavelengths become identical to the reference values given for absorption wavelengths. The correction of the control instructions corrects the angle of the diffraction grating 10, thereby completing the wavelength calibration processes.

The corrected spectrum has the intensity distribution that is free of the ripple at the period of 1 nm to 2 nm and the overall slope. Namely, the intensity distribution of the corrected spectrum is free from the full width at half maximum of the emission band of the reference light and the ripple period thereof. This corrected intensity distribution permits accurate detection of the absorption wavelengths of the acetylene gas. Namely, accurate detection can be made of the difference of the detected absorption wavelengths from the reference values for absorption wavelengths. Therefore, the optical spectrum analyzer is configured to realize the highly accurate wavelength calibration.

As shown in FIG. 6, the acetylene gas has a predetermined plurality of absorption wavelengths. The corrected spectrum has the intensity distribution that has two gentle hillocks. In order to reduce the calibration error, it is preferable to compare the corrected spectrum to the reference values given for absorption wavelengths at the specific wavelengths fa and fb alone or in combination. The specific wavelengths fa and fb are positioned at the centers of the two gentle hillocks of the intensity distribution, respectively. Either one of the specific wavelengths fa and fb can be used for the above-described comparison. For example, if the absorption wavelength fa is used for the wavelength calibration, a difference is detected between the wavelength fa and the given reference value that corresponds to the wavelength fa. The difference of the detected wavelength is used as the amount of calibration to be performed.

Both the specific wavelengths fa and fb can also be used for the above-described comparison. In this case, detections are made for differences of the specific wavelengths fa and fb from the reference values that corresponds to the wavelengths fa and fb, respectively. The average of the detected differences is calculated and used as the amount of calibration to be performed.

Not only the specific wavelengths fa and fb but also other absorption wavelength or wavelengths may be compared to the given reference values corresponding to them, thereby finding differences between them. The average of the detected differences is calculated and used as the amount of calibration to be performed.

As described above, the corrected spectrum may be obtained by calculating the ratio of the observed spectrum to the moving average spectrum. It is possible as a modification to obtain a different observed spectrum after the wavelength resolution of the Czerney-Turner spectrometer was changed. In other words, a different observed spectrum can additionally be obtained at a different wavelength resolution of the Czerney-Turner spectrometer. The different observed spectrum is different from the observed spectrum. The different wavelength resolution is different to the wavelength resolution at which the observed spectrum has been obtained.

The width of the outgoing slit 12 that is included in the Czerney-Turner spectrometer may be adjusted to change the wavelength resolution of the Czerney-Turner spectrometer. After the wavelength resolution was changed, a different observed spectrum is additionally obtained in the same manner as the observed spectrum was obtained at the original wavelength resolution. In other words, a first observed spectrum is obtained in the normal measurement mode where the wavelength resolution has not been changed yet. Further, a second observed spectrum is obtained after the wavelength resolution has been changed. The corrected spectrum may be obtained by calculating a ratio of the first observed spectrum to the second observed spectrum.

Figure 7:
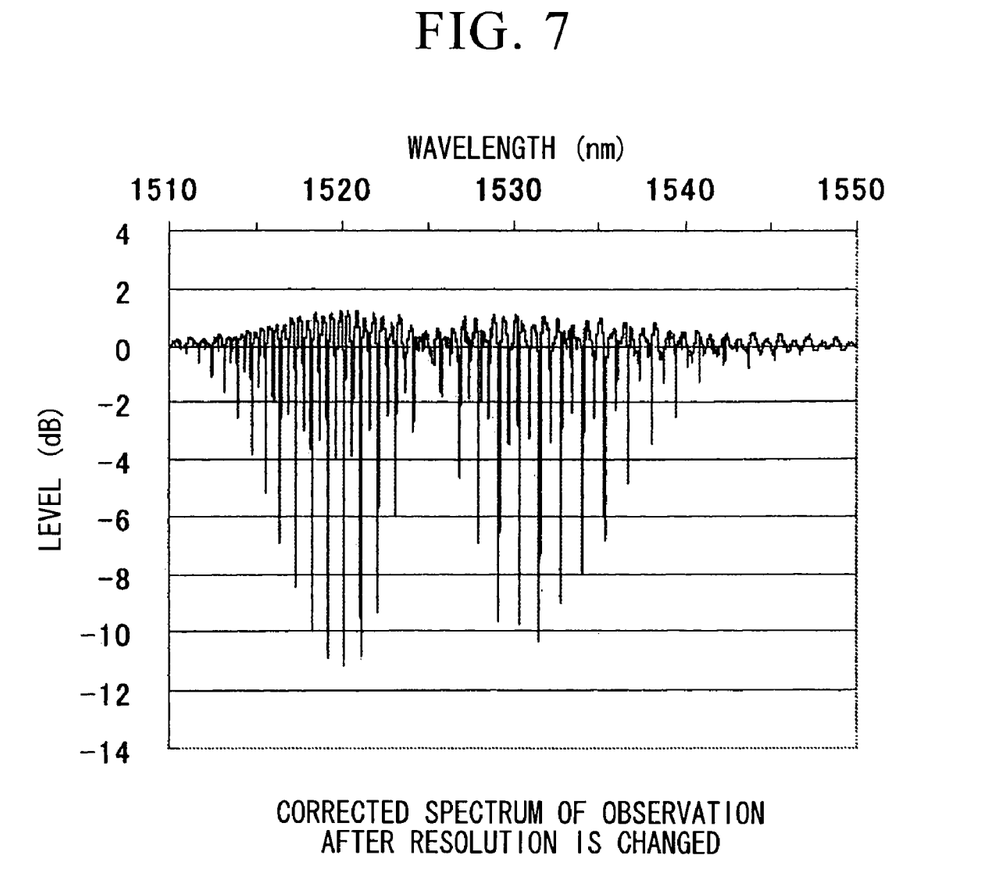
FIG. 7 is a view illustrating a corrected spectrum that is obtained by comparing an observed spectrum where a wavelength resolution is not changed to a different observed spectrum where the wavelength resolution has been changed.

FIG. 7 is a view illustrating a corrected spectrum that is obtained by comparing an observed spectrum to a different observed spectrum. The observed spectrum is obtained where the wavelength resolution has not yet been changed. The different observed spectrum is obtained where the wavelength resolution has been changed. The wavelength resolution of the Czerney-Turner spectrometer is changed so as to be sufficiently larger than the full width at half maximum of approximately 0.02 nm and smaller than a half of the ripple period of 1 nm to 2 nm. After the wavelength resolution of the Czerney-Turner spectrometer has been changed as described above, the different observed spectrum is obtained. This different observed spectrum may play the same role as the above-described moving average spectrum. The corrected spectrum can be obtained by calculating a ratio between the observed spectrum and the different observed spectrum. The corrected spectrum is independent from both the full width at half maximum of the emission band of the reference light and the ripple period.

The above described embodiment may be applied to not only the optical spectrum analyzer but also an apparatus for wavelength separation such as a wavelength monitor.

The term "configured" is used to describe a component, section or part of a device includes hardware and/or software that is constructed and/or programmed to carry out the desired function.

The terms of degree such as "substantially," "about," and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A wavelength calibration method comprising:
   obtaining an observed spectrum of a light that has a wavelength band, the light having at least an attenuated wavelength component that corresponds to at least a predetermined absorption wavelength that is included in the wavelength band;
   obtaining a corrected spectrum from the observed spectrum, the corrected spectrum having reduced dependencies upon the full width at half maximum of an emission band of the light and upon the intensity ripple period of the light; and
   performing a wavelength calibration with reference to the corrected spectrum.

2. The wavelength calibration method according to claim 1, wherein the corrected spectrum is substantially independent from the full width at half maximum and the intensity ripple period.

3. The wavelength calibration method according to claim 1, wherein performing the wavelength calibration comprises:
   obtaining at least a difference between the at least a predetermined absorption wavelength and at least an absorption wavelength of the corrected spectrum; and
   performing the wavelength calibration based on the difference.

4. The wavelength calibration method according to claim 3, wherein the light has a plurality of attenuated wavelength components that corresponds to a plurality of predetermined absorption wavelengths that is included in the wavelength band,
   obtaining the at least a difference comprises obtaining a plurality of differences between the plurality of predetermined absorption wavelengths and a plurality of absorption wavelengths of the corrected spectrum, and
   performing the wavelength calibration comprises performing the wavelength calibration based on the plurality of differences.

5. The wavelength calibration method according to claim 1, wherein obtaining the corrected spectrum comprises:
   performing a moving average process of the observed spectrum to obtain a moving average spectrum; and
   calculating a ratio between the moving average spectrum and the observed spectrum.

6. The wavelength calibration method according to claim 1, wherein obtaining the corrected spectrum comprises:
   obtaining a different observed spectrum of the light at a different wavelength resolution that is larger than the full width at half maximum and smaller than a half of the intensity ripple period, the different wavelength resolution being different from a wavelength resolution at which the observed spectrum is obtained; and
   calculating a ratio between the different observed spectrum and the observed spectrum.

7. The wavelength calibration method according to claim 1, wherein obtaining the observed spectrum comprises:
   emitting the light from a light emitting diode; and
   transmitting the light through a gas absorption cell that is configured to absorb the light at the at least a predetermined absorption wavelength.

8. The wavelength calibration method according to claim 7, wherein the gas absorption cell is filled with a gas that has a plurality of predetermined absorption wavelengths,
   performing the wavelength calibration further comprises:
   obtaining at least two differences between at least two absorption wavelengths of the plurality of predetermined absorption wavelengths and at least two absorption wavelengths of the corrected spectrum; and
   performing the wavelength calibration based on the at least two differences.

9. A wavelength calibration apparatus comprising:
   an optical system configured to obtain a wavelength-separated light from a light, the light has a wavelength band, the light having at least an attenuated wavelength component that corresponds to at least a predetermined absorption wavelength that is included in the wavelength band; and
   a control system configured to obtain an observed spectrum of the light from the wavelength-separated light, the control system being configured to obtain a corrected spectrum from the observed spectrum, the corrected spectrum having reduced dependencies upon the full width at half maximum of an emission band of the light and upon an intensity ripple period of the light, the control system being configured to perform a wavelength calibration with reference to the corrected spectrum.

10. The wavelength calibration apparatus according to claim 9, wherein the corrected spectrum is substantially independent from the full width at half maximum and the intensity ripple period.

11. The wavelength calibration apparatus according to claim 9, wherein the control system is configured to obtain at least a difference between the at least a predetermined absorption wavelength and at least an absorption wavelength of the corrected spectrum, and
   the control system is configured to perform the wavelength calibration based on the difference.

12. The wavelength calibration apparatus according to claim 11, wherein the light has a plurality of attenuated wavelength components that corresponds to a plurality of predetermined absorption wavelengths that is included in the wavelength band,
   the control system is configured to obtain a plurality of differences between the plurality of predetermined absorption wavelengths and a plurality of absorption wavelengths of the corrected spectrum, and the control system is configured to perform the wavelength calibration based on the plurality of differences.

13. The wavelength calibration apparatus according to claim 9, wherein the control system is configured to perform a moving average process of the observed spectrum to obtain a moving average spectrum, and the control system is configured to calculate a ratio between the moving average spectrum and the observed spectrum.

14. The wavelength calibration apparatus according to claim 9, wherein the control system is configured to obtain a different observed spectrum of the light at a different wavelength resolution that is larger than the full width at half maximum and smaller than a half of the intensity ripple period, the different wavelength resolution is different from a wavelength resolution at which the observed spectrum is obtained, and the control system is configured to calculate a ratio between the different observed spectrum and the observed spectrum.

15. The wavelength calibration apparatus according to claim 9, wherein the optical system further comprises:

a light emitting diode that emits the light;

a gas absorption cell disposed to allow the light to be transmitted through the gas absorption cell, the gas absorption cell being configured to absorb the light at the at least a predetermined absorption wavelength;

a spectrometer configured to convert the light that has been transmitted through the gas absorption cell into a wavelength-separated light that has wavelength components; and an optical detector configured to detect the intensity of the wavelength-separated light to generate a light intensity detection signal.

16. The wavelength calibration apparatus according to claim 15, wherein the gas absorption cell is filled with a gas that has a plurality of predetermined absorption wavelengths, the control system is configured to obtain at least two differences between at least two absorption wavelengths of the plurality of predetermined absorption wavelengths and at least two absorption wavelengths of the corrected spectrum, and the control system is configured to perform the wavelength calibration based on the at least two differences.

* * * * *